United States Patent [19]
Brigati

[11] Patent Number: 4,798,706
[45] Date of Patent: Jan. 17, 1989

[54] DEVICE FOR HOLDING HORIZONTAL ARRAY OF LIQUID ALIQUOTS

[75] Inventor: David J. Brigati, Hummelstown, Pa.

[73] Assignee: Fisher Scientific Co., Pittsburgh, Pa.

[21] Appl. No.: 32,875

[22] Filed: Mar. 31, 1987

Related U.S. Application Data

[63] Continuation-in-part of Ser. No. 775,864, Sep. 13, 1985, Pat. No. 4,731,335.

[51] Int. Cl.⁴ .......................... C12M 1/18; B01L 3/00
[52] U.S. Cl. ...................................... 422/102; 206/84; 350/536; 435/293; 435/301
[58] Field of Search .................... 422/63, 66, 102, 104, 422/61; 435/293, 301; 206/0.83, 0.84; 350/536

[56] References Cited

U.S. PATENT DOCUMENTS

| | | | |
|---|---|---|---|
| 2,119,773 | 6/1938 | Buckner | 206/0.84 |
| 3,005,375 | 10/1961 | Sherman | 350/536 |
| 3,656,833 | 4/1972 | Wallace | 350/536 |
| 3,736,042 | 5/1973 | Markovitz et al. | 350/536 |
| 3,904,781 | 9/1975 | Henry | 350/536 |
| 4,441,793 | 4/1984 | Elkins | 350/536 |
| 4,518,565 | 5/1985 | Boger et al. | 422/104 |

Primary Examiner—Michael S. Marcus
Attorney, Agent, or Firm—Alan M. Doernberg

[57] ABSTRACT

A device for holding a horizontal array of discrete aliquots of treating liquid having,
(a) a horizontally-extending rigid base,
(b) a horizontally-extending elastomeric member (or coating) on the horizontally-extending rigid base with a substantially planar horizontally-extending upper surface, and
(c) a plurality of recesses formed in the elastomeric member, each recess opening to the horizontally-extending upper surface, the elastomeric member (or coating) having at its upper surface a material sufficiently incompatible with the treating liquid for a discrete aliquot of treating liquid in a recess to form a convex shape extending above the plane of the adjacent upper surface of the elastomeric member (or coating).

11 Claims, 4 Drawing Sheets

DEVICE FOR HOLDING HORIZONTAL ARRAY OF LIQUID ALIQUOTS

This is a continuation-in-part of U.S. Ser. No. 775,864 of Brigati, filed Sept. 13, 1985, copending and commonly assigned now U.S. Pat. No. 4,731,335.

The present invention relates to devices for holding a plurality of discrete aliquots of liquid in a fixed horizontal array. Such a device is particularly useful in methods where the aliquots are contacted simultaneously from above by the edges of gaps of a size whereby the liquid is drawn by capillary action into the gaps. Such a method is described in more detail in U.S. Ser. No. 775,864, the disclosure of which is incorporated herein by reference.

SUMMARY OF THE INVENTION

The present invention provides a device for holding a horizontal array of discrete aliquots of treating liquid comprising:

(a) a horizontally-extending rigid base, (b) a horizontally-extending elastomeric member on the horizontally-extending rigid base, the elastomeric member having a substantially planar horizontally-extending upper surface, and (c) a plurality of recesses formed in the elastomeric member, each recess opening to the horizontally-extending upper surface, the elastomeric member having at its upper surface a material sufficiently incompatible with the treating liquid for a discrete aliquot of treating liquid in a recess to form a convex shape extending above the plane of the adjacent upper surface of the elastomeric member.

The present invention further provides a device for holding a horizontal array of discrete aliquots of a treating liquid comprising:

(a) a horizontally-extending rigid base, (b) a coating on the horizontally-extending rigid base, the coating having a substantially planar horizontally-extending upper surface, and (c) a plurality of recesses formed in the coating, each recess opening to the horizontally-extending upper surface, the coating having at its upper surface a material sufficiently incompatible with the treating liquid for a discrete aliquot of treating liquid in a recess to form a convex shape extending above the plane of the adjacent upper surface of the coating.

DETAILED DESCRIPTION OF THE INVENTION

Figure 1:
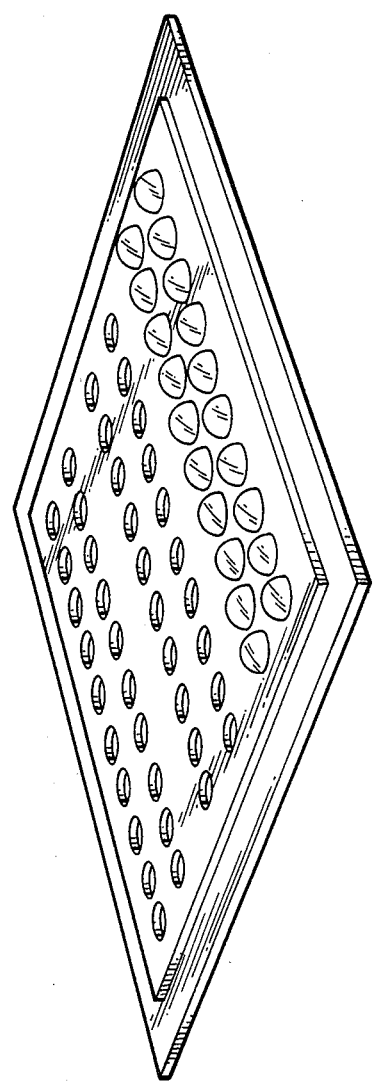
FIG. 1 is a perspective view of a droplet holder according to a first embodiment of the invention, and corresponds to FIG. 7 of U.S. Ser. No. 775,864.

FIG. 1 illustrates a first embodiment of the present device. A rigid horizontally-extending base 462 supports a horizontally-extending elastomeric member 464. Sixty holes of circular cross-section are provided through member 464 in three double rows of ten. As illustrated, the first double row of ten is filled with twenty droplets of a first treating liquid, including droplets 468a, 468j, 469a and 469j. The second double row of holes, including holes 466k and 466t is empty. The third double row at holes, including holes 466dd and 466u is empty. As indicated below, each double row of holes can be filled with a different treating liquid.

The base 462 underlies the entire elastomeric member 464. Each pair of holes (e.g., the pair filled with droplets 468j and 469j) is arranged to simultaneously contact a gap between two one-inch wide microscope slides. Accordingly, the horizontal distance from the near edge of droplet 468j to the far edge of droplet 469j is desirably less than one inch (25.4 mm). The spacing between droplet pairs should be sufficient to maintain discreteness. Thus, for example, the separation between droplet 468j and droplet 468i depends upon the degree of incompatability between the liquid and the elastomer 464 and can be as little as one millimeter if the incompatability is strong enough. Preferably, this distance is at least 2 mm to accommodate various liquids.

Figures 2A, 2B:
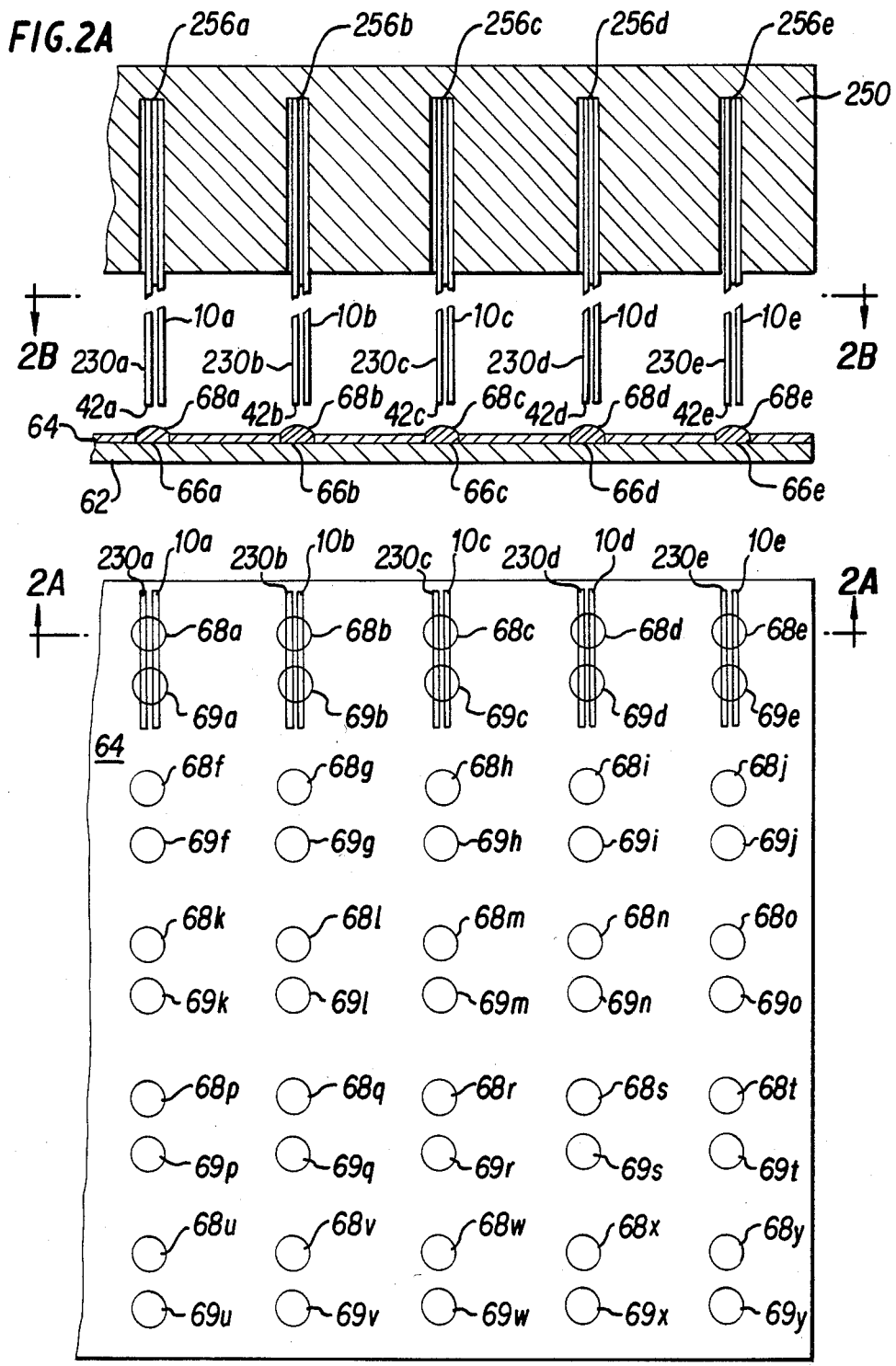
FIG. 2A is a side view, taken along section line 2A—2A in FIG. 2B, of an array of slide assemblies above a droplet holder, the droplet holder being in accordance with a second embodiment of the invention.
FIG. 2B is a top plan view of the droplet holder device shown in section in FIG. 2A, taken along line 2B—2B in FIG. 2A.

FIGS. 2A and 2B show how an array of twenty-five slide pairs can be aligned and used in accordance with the method of U.S. Ser. No. 775,864 to contact a device according to a second embodiment of the present invention. Referring to FIG. 2A, one row of five slide pairs is shown. Each first slide (10a, 10b, 10c, 10d, 10e) is spaced from a second or facing slide (230a, 230b, 230c, 230d and 230e) by a shim. Vertical alignment is maintained by the upper edges (256a, 256b, 256c, 256d and 256e) of five recesses formed in the bottom face of holder 250.

Thus, vertically-extending gaps of the thickness of the shim are formed in each slide pair, as described in relation to FIGS. 2A and 2B of U.S. Ser. No. 775,864, terminating in lower spaces 42a, 42b, 42c, 42d and 42e between, respectively, aligned first and second lower edges of the first and facing slides 10a/230a, 10b/230b, 10c/230c, 10d/230d and 10e/230e. All sets of lower edges are in a common horizontal plane a fixed distance below the lower face of holder 250.

A droplet holder is located below this horizontal plane, consisting of a rigid base 62 and a horizontally-extending elastomeric member 64. As shown in FIG. 2A, five holes 66a through 66e are formed in and through elastomeric member 64, and these holes are filled with discrete aliquots or droplets 68a through 68e, respectively, each of defined volume, e.g. 100 microliters. As described more fully below, each droplet 68a-68e projects above the top face of elastomeric member 64. The alignment is such that, when the slide holder 250 is lowered, lower spaces 42a-42e are contacted by the upper portions of droplets 66a through 66e, respectively. The droplets are normally introduced into the droplet holder from above (e.g., by a micropipetting device), but can also be introduced from below by means of a narrow passage formed in rigid base 62.

Referring to FIG. 2B, the top of elastomeric member 64 can be seen with five double rows of droplets 68a-68y and 69a-69y. Looking at the profiles of slides 10a-10e, with facing slides 230a-230e, it can be seen that they will contact droplets 68a-68e and 69a-69e, with, for example, lower space 42a contacting droplets 68a and 69a near the two ends of lower space 42a.

Just as the one row of slide pairs 10a/230a through 10e/230e contacts droplets 68a-68e and 69a-69e, four additional rows of five slide pairs each can be aligned within holder 250 so as to contact, respectively:(2) droplets 68f-68j and 69f-69j, (3) droplets 68k-68o and 69k-69o, (4) 68p-68t, and 69p-69t, and (5) 68u-68y and 69 u-69y. Because the lower edges of all first slides, facing slides and thus lower spaces can be held in precise alignment within a common horizontal plane, and elastomeric member 64 holds the entire array of droplets in precise alignment within a common horizontal plane, one can reproducibly contact each lower space between first and second lower edges of a first and facing slide, respectively, with two droplets. Furthermore, the discreteness of droplets 68a-68y and 69a-69y enables differently than each other first slide as to treating liquid applied. The effect of space 42a (between first lower edge 14a and second lower edge 234a of slides 10a and 230a) being contacted by a droplet in hole 66a is shown in FIG. 3C of U.S. Ser. No. 775,864. A capillary column of liquid 70a rises in the capillary gap by capillary action. This effect is enhanced by the relative incompatibility of the liquid with the surface of elastomeric member 64, e.g., because the aqueous droplet is repelled by the hydrophobic surface of elastomeric member 64. Such incompatibility (evidenced by beading of the treatment liquid if it were placed on a flat surface of elastomeric material used for member 64) also causes the droplets to stand above the top surface of member 64.

After the capillary column has risen as far as capillary action will take it (typically about 30 to 40 mm in the indicated gap of 0.15 mm), the slide assembly can be lifted by holder 250 away from elastomeric member 64. Each slide pair (e.g., 10a/230a) will hold, by capillary action, the treating liquid received from the droplets (e.g., 68a and 69a) with which its lower space (e.g., 42a) has been contacted. After the liquid has remained in the gap for a desired time period, the slide assembly is now lowered onto an absorbent material as shown in FIG. 3D of U.S. Ser. No. 774,864. Since the liquid is more compatible with the absorbent material than with the surfaces of slides 10a and 230a, now the capillary column will descend, with the treating liquid spreading downward and outwardly as a liquid front within the absorbent material. Within a matter of seconds, the gap between the slide pair will be evacuated essentially completely of liquid by such capillary action, except perhaps for minute amounts that may adhere to the sample or to other hygroscopic surfaces along the slide gap 240 or lower edges 14a and 234a. Once the liquid is evacuated from the slide gap 240, the slide pair may now be moved to another droplet holder, or to a sheet or bath of treating liquid for the next step.

In order to maintain the droplets as discrete aliquots, it is desirable to maintain a spacing between droplets and between slide pairs. Looking again at FIG. 2A, droplets 66a and 66b should be sufficiently spaced from each other to remain discrete and not intermix. This discreteness is especially important when the flexibility is desired to use different treating liquids on slide pair 10a/230a than on slide pair 10b/230b. This would occur, for example, if twenty-five different primary antibodies are being used on the device shown in FIG. 2B. Conventionally, each slide (e.g., slide 10a) is one inch (25.4 mm) wide and one millimeter thick. It is then desirable for the spacing between slide 10a and slide 230b to be at least 5 mm. In such case, the droplets would be separated by a minimum distance of 7 mm (e.g., the distance from the center of droplet 68a to the center of droplet 68b). While this distance may be much larger than 7 mm (as illustrated), it is now preferred that this spacing be no more than 15 mm, and preferably be about 7 to about 10 mm.

Figure 3A:
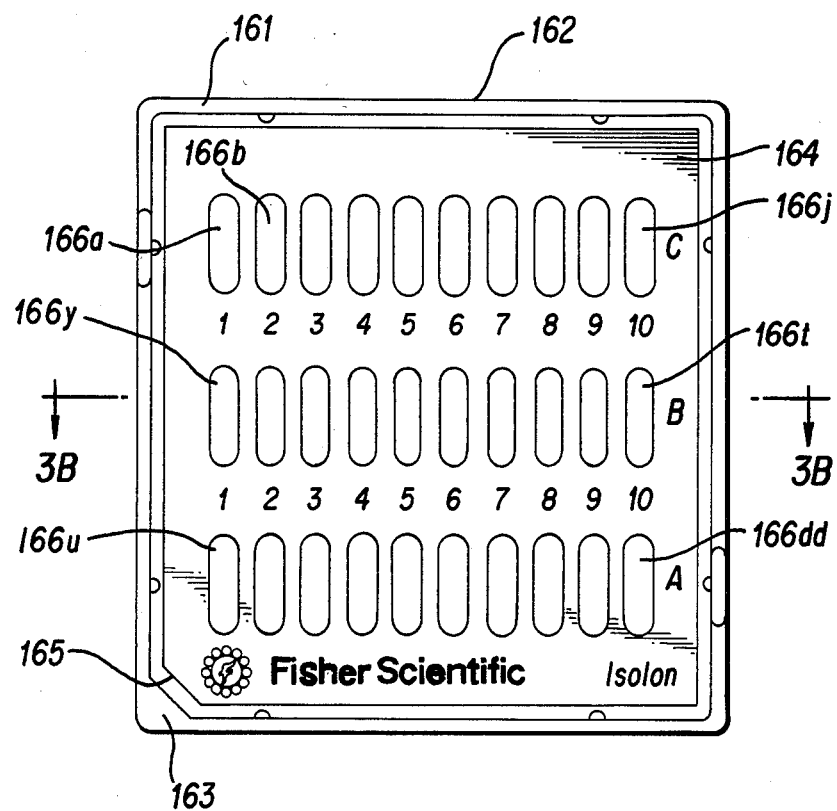
FIG. 3A is a top plan view of a device according to a third embodiment of the present invention.

FIG. 3A illustrates a device according to a third embodiment of the invention wherein elastomeric member 164 is fitted on rigid base 162. Rigid base 162 is in the form of a square dish, with a flat surface on which elastomeric member 164 sits and upstanding walls 161 which surround and align elastomeric member 164. An angle 165 is formed in a corner of elastomeric member 164. A corresponding angle 163 in the upstanding walls 161 of base 162 assures that elastomeric member 164 is correctly positioned.

Indicia (numerals 1 through 10 and letters A, B and C) are Provided on the top face of elastomeric member 164. Thirty oblong holes are provided through elastomeric member 164 in three rows of ten. Accordingly, the top left hole 166a is recognizable as C1. It corresponds to droplets 68a and 69a in FIG. 2B and to droplets 468a and 469a in FIG. 1. In similar fashion, oblong hole 166j is recognizable as C10 and corresponds to droplets 468j and 469j in FIG. 1, oblong hole 166k is recognizable as B1 and corresponds to holes 466k; oblong hole 166t is recognizable as B10 and corresponds to holes 466t; oblong hole 166u is recognizable as A1 and corresponds to holes 466u; oblong hole 166dd is recognizable as A10 and corresponds to holes 466dd.

Since each of oblong holes 166a-166dd is intended to provide liquid for a slide pair, the length of the hole in a horizontal direction is preferably not greater than the width of the slides (typically one inch or 25.4 mm). Preferably, each oblong hole is 10-25 mm (especially 15-20 mm) in such horizontal length. The horizontal spacing between adjacent oblong holes in a row should be sufficient to maintain discreteness. As illustrated, such adjacent oblong holes (e.g., holes 166a and 166b) are spaced by 0.1225 inch (3.1 mm) at closest points. Each oblong hole is illustrated as 0.19 inch (4.8 mm) in width. Therefore, as illustrated, the total distance from one oblong hole to the next, center to center, is 0.3125 inch (7.9 mm). As with the round holes of FIG. 2A, this distance is preferably about 7-10 mm.

Figure 3B:
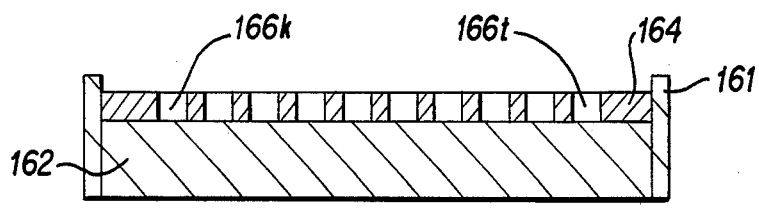
FIG. 3B is an elevational view, in section, taken along line 3B—3B in FIG. 3A.
Figure 3C:
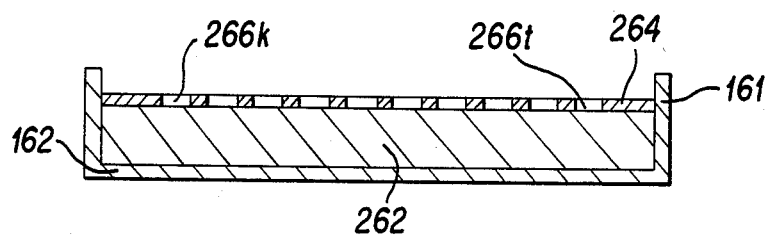
FIG. 3C is an elevational view, in section, similar to FIG. 3B, of a droplet holder device according to a fourth embodiment of the invention.

FIG. 3B shows a cross-section of the device of FIG. 3A. Each oblong hole (e.g.. 166t) can be seen to extend from the top surface of elastomeric member 164 through the elastomeric member 164 down to the top surface of rigid base 162. The sealing of the bottom of elastomeric member 164 to the top surface of rigid base 162 can also be seen.

It should be appreciated that the width of the oblong holes is dictated somewhat by the desired volume of treating liquid in each aliquot. In a device similar to that of FIG. 3B, but with a rigid coating 164 of thickness one millimeter, each oblong hole of 0.69 inch (17.5 mm) length and 0.19 inch (4.8 mm) width held 150-200 microliters of liquid, with liquid standing above the top surface. By making the thickness of member 164 greater (e.g., 3 mm), one can either accommodate greater volumes or reduce the width (to, e.g., 2-3 mm). With member 164 being elastomeric, the liquid need not necessarily stand up above the top surface; when each slide pair is lowered, it depresses the elastomeric member somewhat and can thus draw liquid upward even if the initial liquid level is at or slightly above the plan of the top surface of member 164. The sealing of the bottom of member 164 to the top of base 162 can be achieved by gluing or lamination, but flexible elastomeric members can also be freely removable without attachment.

FIG. 3C shows an additional embodiment wherein the elastomeric member 164 has been replaced by a polymer coating 264 on a rigid glass (or hard plastic) base 262. The sandwich structure 262/264 is placed inside of element 162, which now serves merely as a tray. The top view of this device would look identical to FIG. 3A. Because the coating 264 is relatively thin (typically 10-20 micrometers), the capacity of each oblong hole (e.g., 266k and 266t) is reduced. The polymer used for coating 264 is chosen to be incompatible with treating liquid (e.g., hydrophobic for aqueous treating liquids) so as to cause the liquid to stand up in a convex shape above the top surface of polymer coating 264. The coating may be permanent or removable by washing so that the surface is respectively reusable or disposable.

As illustrated by comparing FIGS. 1, 2A and 2B to FIG. 3A, one or more holes can be provided for each capillary gap. In each illustrated embodiment, the holes extend vertically through the elastomeric member so that liquid contacts the base. While such holes are preferred, the elastomeric member (or coating) could alternatively be provided with recesses which communicate only with the top surface of the member. The figures illustrate arrangements of holders for either three rows of ten slide pairs or five rows of five slide pairs. Other permutations are contemplated, especially five rows of ten slide pairs provided by five rows of ten oblong holes.

The devices shown in the figures are filled by feeding liquid from the top into each hole, either sequentially or concurrently. Thus, an automatic pipette could be used to fill each hole in row A or each hole in column 1 with a first liquid. Next, each other row (or column) could be filled with the same or different liquid. As described more fully in U.S. Ser. No. 775,864, each such liquid could provide an antibody, a nucleic acid probe, an enzyme, a chromogen or other reagent. Furthermore, each liquid could represent a sample (of, for example, serum or urine) to be drawn by the capillary gap into contact with an immobilized antibody or immobilized antigen. In a multi-step process (analogous to that described in reference to FIG. 6 of U.S. Ser. No. 775,864), the slide may then be contacted with a series of reagents to obtain an analysis of the sample for, respectively, the corresponding antigen or antibody.

It is also contemplated to provide passages in the rigid base to feed treating liquid (or liquid sample) into each hole from below. Thus, for example, a reservoir of liquid could be connected through passages in the rigid base to one or a plurality of the holes. By height adjustment of the reservoir or precise pressure or volume control on the reservoir, liquid would flow into each connected hole and fill to a height just above the coating surface or surface of the elastomeric member. Once liquid was removed from such hole or holes by capillary action into a gap or gaps, the continued or renewed replacement of volume would refill the hole or holes to the same level automatically.

Figure 4:
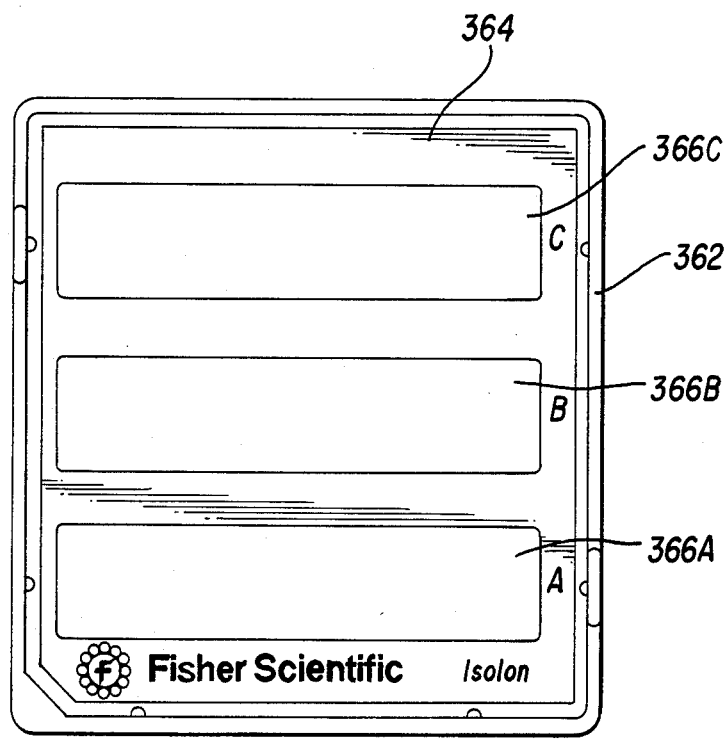
FIG. 4 is a top plan view, similar to FIG. 3A, of a droplet holder according to a fifth embodiment of the present invention.

FIG. 4 shows an additional embodiment of the present invention wherein three long liquid compartments are provided in rows 366A, 366B and 366C designated by indicia as A, B and C. Such a holder, formed either from an elastomeric member 364 on a rigid base 362 or a coating 364 on a rigid base 362 maintains and isolates three aliquots of treating liquid which may be the same or different. Such a holder could be used, for example, in a step of the multi-step process described in U.S. Ser. No. 775,864 where samples have already been contacted with primary antibody, and three different labeled secondary antibodies are to be used (e.g., anti-IgG, anti-IgM and goat-anti-mouse antibody). A similar device with ten slots extending in a transverse direction could be used, for example, if at an earlier stage in the process, ten different primary antibodies were to be tested, each of which is known to be a mouse antibody but is of unknown subclass (IgG, IgM or other).

What is claimed is:

1. A device for holding a horizontal array of discrete aliquots of treating liquid consisting essentially of:
   (a) a horizontally-extending rigid base,
   (b) a horizontally-extending elastomeric member on the horizontally-extending rigid base, the elastomeric member having a substantially planar horizontally-extending upper surface, and
   (c) a plurality of recesses formed in the elastomeric member, each recess being sized to receive internally only microliter quantities of a treating liquid and opening to the horizontally-extending upper surface, the elastomeric member having at its upper surface a material sufficiently incompatible with an aqueous treating liquid for a discrete aliquot of treating liquid of small volume greater than the internal volume of a recess to form a convex shape extending from within a recess above the plane of the adjacent upper surface of the elastomeric member.

2. The device of claim 1 wherein each recess extends vertically through the elastomeric member and wherein the elastomeric member around each recess is sealed to the rigid base.

3. The device of claim 2 wherein each recess is circular in horizontal cross-section.

4. The device of claim 2 wherein each recess has an elliptical horizontal cross-section with a major axis extending in a first direction.

5. The device of claim 4 wherein each recess is separated in a horizontal direction normal to the first direction from an adjacent recess by at least one millimeter.

6. The device of claim 1 wherein each recess is separated from an adjacent recess in each horizontal direction by at least one millimeter.

7. The device of claim 1 wherein the elastomeric member is separable from the rigid base.

8. A device for holding a horizontal array of discrete aliquots of treating liquid consisting essentially of:
   (a) a horizontally-extending rigid base,
   (b) a horizontally-extending elastomeric member on the horizontally-extending rigid base, the elastomeric member having a substantially planar horizontally-extending upper surface,
   (c) a plurality of recesses formed in the elastomeric member, each recess being sized to receive internally only microliter quantities of a treating liquid and opening to the horizontally-extending upper surface, the elastomeric member having at its upper surface a material sufficiently incompatible with an aqueous treating liquid for a discrete aliquot of treating liquid of small volume greater than the internal volume of a recess to form a convex shape extending from within a recess above the plane of the adjacent upper surface of the elastomeric member, and (d) a holder under the horizontally-extending rigid base, the unitary horizontally-extending rigid base and horizontally-extending elastomeric member being removable from the holder.

9. The device of claim 8 wherein each recess has an elliptical horizontal cross-section with a major axis extending in a first direction.

10. The device of claim 9 wherein each recess is separated in a horizontal direction normal to the first direction from an adjacent recess by at least one milimeter.

11. The device of claim 8 wherein each recess is separated from an adjacent recess in each horizontal direction by at least one millimeter.

* * * * *